United States Patent [19]

Luther et al.

[11] Patent Number: 4,702,735
[45] Date of Patent: Oct. 27, 1987

[54] ASSEMBLY OF BREAKAWAY NEEDLE AND CATHETER

[75] Inventors: Ronald B. Luther, Newport Beach, Calif.; Daniel R. Snyder; Craig M. Whitehouse, both of Branford, Conn.

[73] Assignee: DRS Infusion Systems, Inc., Branford, Conn.

[21] Appl. No.: 811,807

[22] Filed: Dec. 20, 1985

[51] Int. Cl.$^4$ .............................................. A61M 5/18
[52] U.S. Cl. ..................................... 604/161; 604/165
[58] Field of Search ............... 604/158, 161, 163, 165, 604/171, 272

[56] References Cited

U.S. PATENT DOCUMENTS

| | | | |
|---|---|---|---|
| 3,382,872 | 5/1968 | Rubin | 604/161 |
| 3,537,451 | 11/1970 | Beck | 604/165 |
| 3,766,915 | 10/1973 | Rychlik | 604/161 |
| 3,774,605 | 11/1973 | Jewett | 604/161 |
| 4,147,165 | 4/1979 | Tauschinski | 604/161 |
| 4,300,553 | 11/1981 | Seberg | 604/165 |
| 4,377,163 | 3/1983 | Feathers | 128/205.22 |
| 4,449,973 | 5/1984 | Luther | 604/272 |

Primary Examiner—Stephen C. Pellegrino
Assistant Examiner—Mark Rooney
Attorney, Agent, or Firm—Workman, Nydegger & Jensen

[57] ABSTRACT

An assembly of a breakaway needle and catheter is provided for injection by the user, using only one hand. The needle and catheter are inserted by the user, and the needle is then retracted from the puncture site leaving the catheter in place. As the needle is retracted, it breaks apart and separates from the catheter.

The assembly includes adhesive coated taping wings to which the catheter is attached. Hence, when the taping wings are attached to the user's body following splitting of the needle, the catheter will be secured in place for long term use.

5 Claims, 9 Drawing Figures

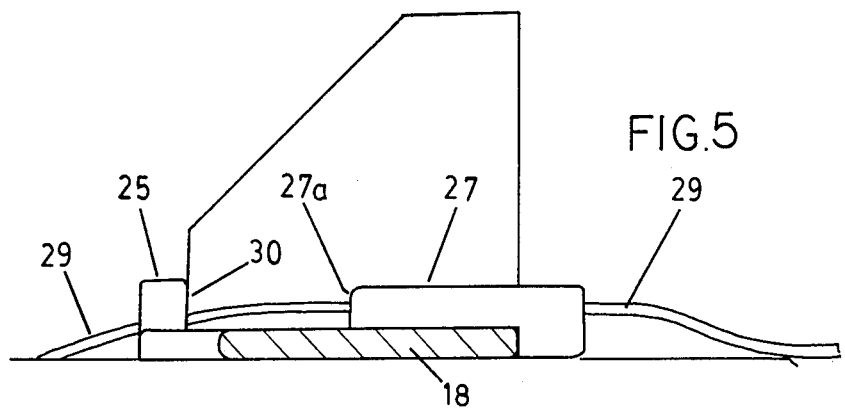
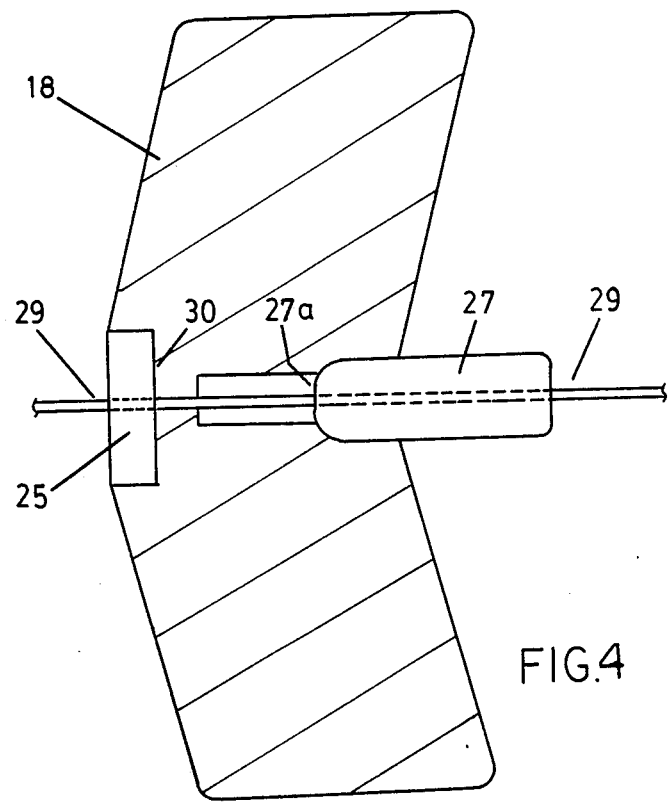

ASSEMBLY OF BREAKAWAY NEEDLE AND CATHETER

BACKGROUND OF THE INVENTION

This invention relates to a new and improved assembly of a breakaway cannula needle and a catheter suitable for insertion by a user and requiring only one hand.

Frequently, individuals must have an injection of a particular drug or pharmaceutical, although the injection need not be given by a physician or a nurse, or even at a hospital. Occasionally, the injection is carried out over a period of time using an infusion pump, and the liquid drug is supplied from a package which is then discarded when empty.

In either event, it is important that the user be able to self-administer the injection. Hence, a device that can be manipulated with one hand is preferred, since it would give the user a wide latitude for selecting an injection site and angle of penetration.

Manipulation of an injection needle with one hand would also enable the user to employ the free hand for other tasks related to use of the device.

Also, it would be preferred to employ a breakaway cannula needle that is inexpensive and can be easily separated from the catheter.

Two types of such breakaway needles are disclosed in U.S. Pat. Nos. 4,449,973 and 4,377,163, and are incorporated herein, by reference. However, these needles, as well as others, generally require injection by a doctor, nurse, etc., since they need both hands to separate the needle halves from the catheter.

In addition, it would be desireable to enable the user to insert the catheter into a puncture site with little or no manipulation of the catheter.

Following insertion of the catheter, it would be desireable to provide a simple menas for attaching the catheter to the user or patient and secure it in place for the duration of the injection period.

THE INVENTION

According to the invention, there is provided a method and assembly of a needle and catheter for injection into a puncture site and insertion of a catheter therein, the catheter being supported on taping wings. The needle bearing the catheter is inserted into the puncture site with one hand; following retraction of the needle, the end portion of the catheter remains in place in the puncture site. As the needle is retracted, it is broken apart and separated from the catheter. The taping wings bearing the catheter are attached to the user's body, and this arrangement enables the catheter to remain fixed in place for the duration of the injection procedure.

Preferably, the cannula employs a breakaway cannula needle, of the type described, in which each breakaway wing of the needle is provided with an extension bearing a large opening through which a user's finger is inserted. This enables the user to manipulate the needle using only one hand. The catheter portion of the assembly is prepositioned within, and extends to the tip of the cannula. The needle with the catheter inserted therein are both mounted on the upper side of the taping wings; the lower side of the wings bear an adhesive that is coated with a removeable label.

Just prior to use, the label is removed from the underside of the taping wings, and the cannula is inserted into the puncture site. Consequently, the catheter which extends to the tip of the needle, will also extend into the puncture site. When the cannula needle is withdrawn, it will split along the upper side of the wings and the catheter will remain in place in the puncture site. The exposed adhesive on the underside of the wings will secure the wings (and hence the attached catheter) to the user during a subsequent injection procedure.

BRIEF DESCRIPTION OF THE DRAWINGS

FIG. 4 is an upper plan view of the assembly following removal of the needle;

FIG. 5 is a side elevation view in axial section showing the catheter engaging the taping wings of the assembly; and, FIGS. 6-9 show the steps of exposing an adhesive side of the taping wings and then inserting, withdrawing and splitting the needle from the catheter.

Figure 1:
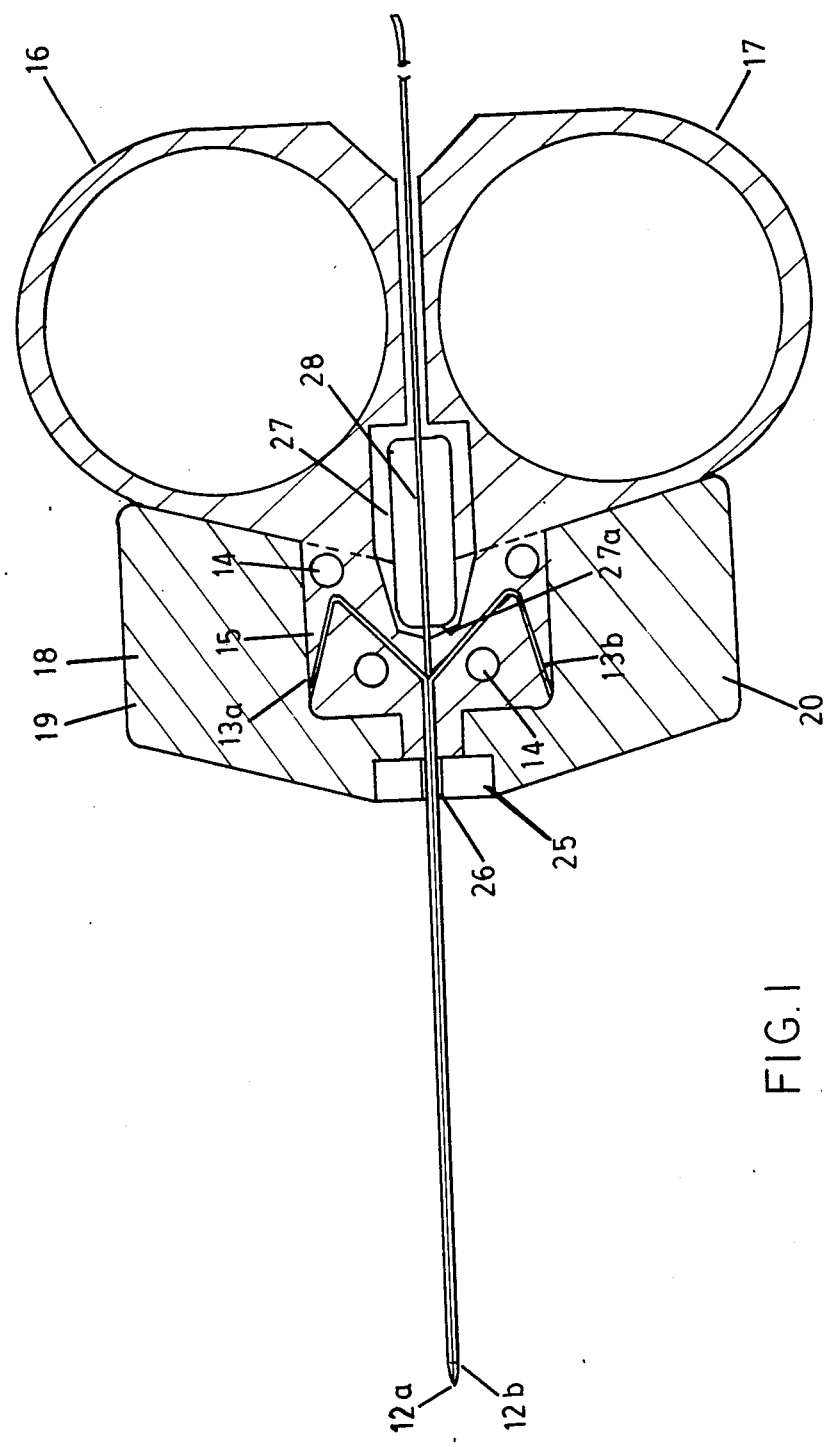
FIG. 1 is an upper plan view showing the cannula and catheter assembly of this invention.
Figure 2:
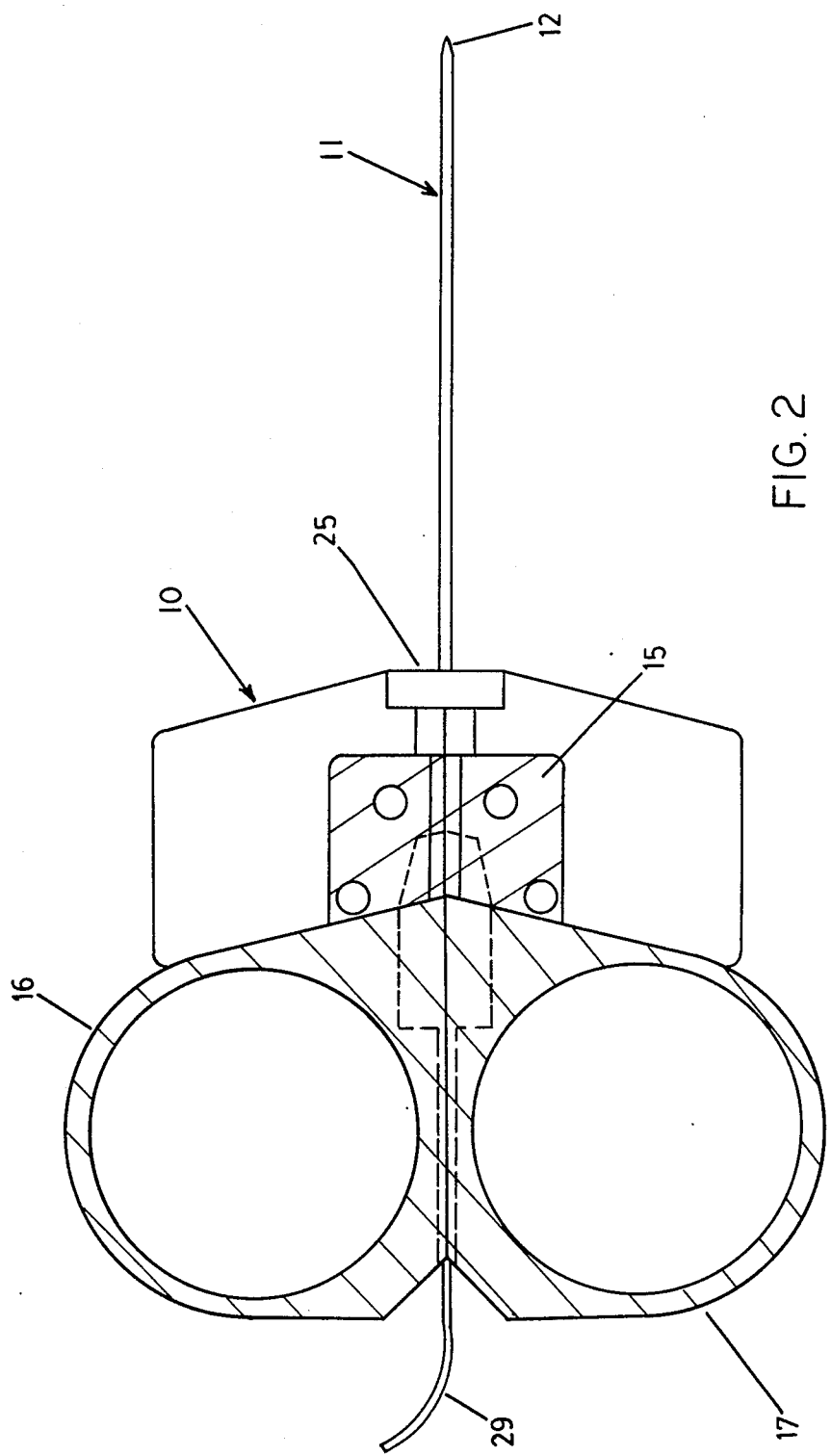
FIG. 2 is a lower plan view of the cannula and catheter of this invention.
Figure 3:
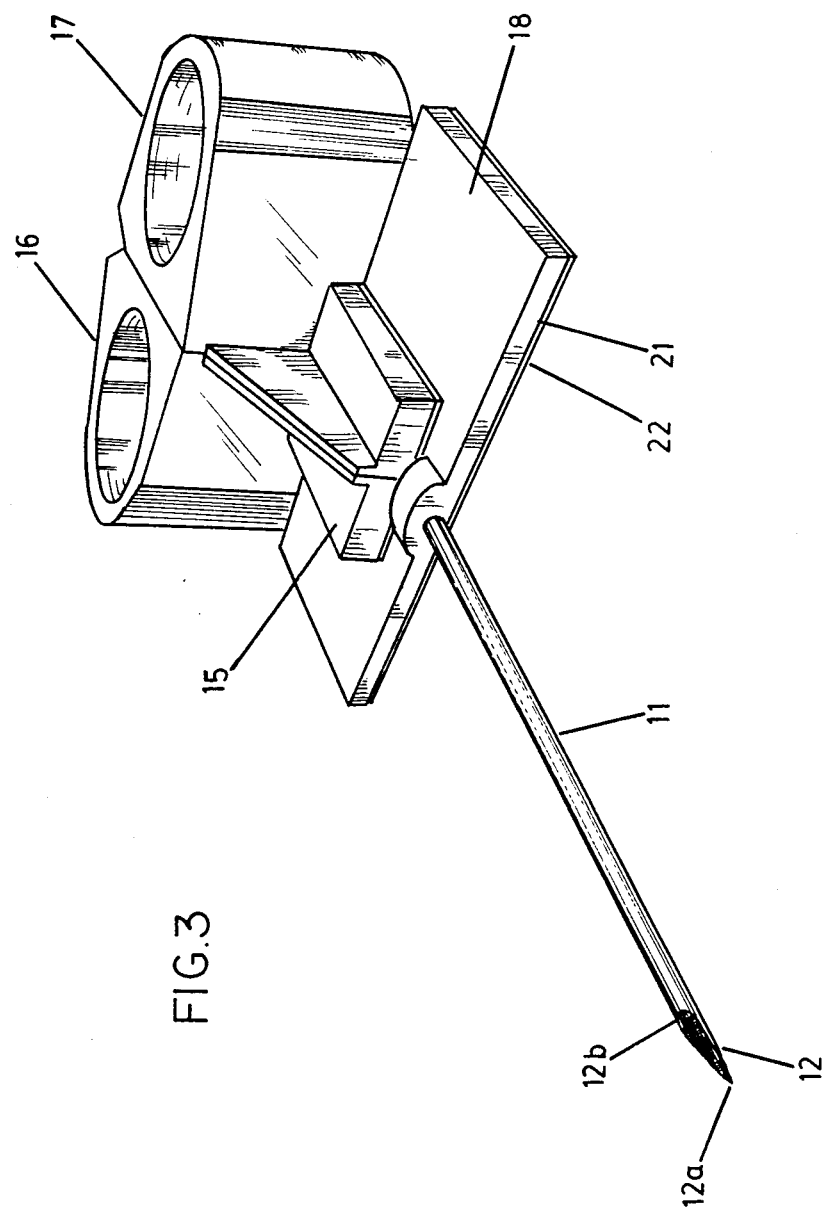
FIG. 3 is an external perspective view of the cannula and catheter assembly of this invention.
Figure 7:
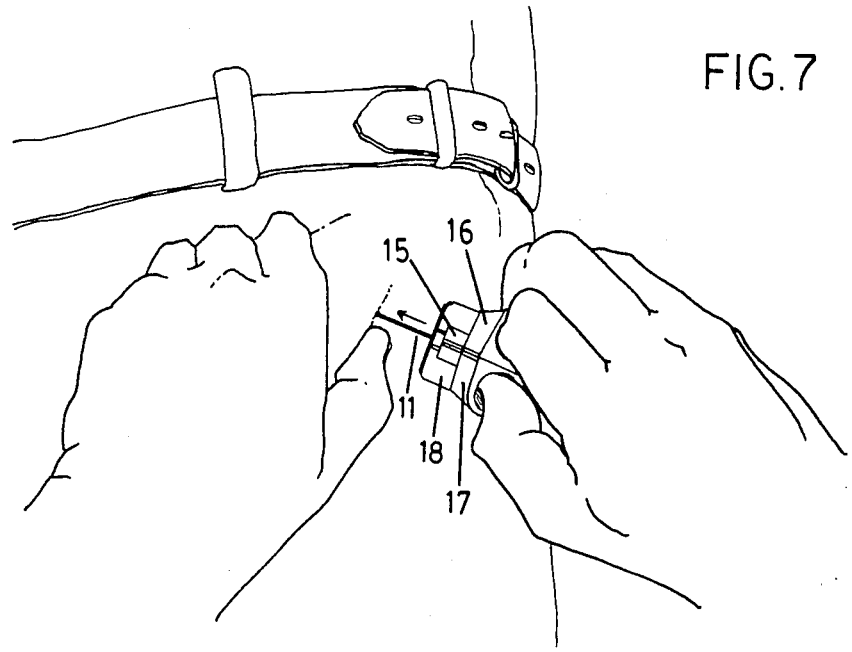
Figure 6:
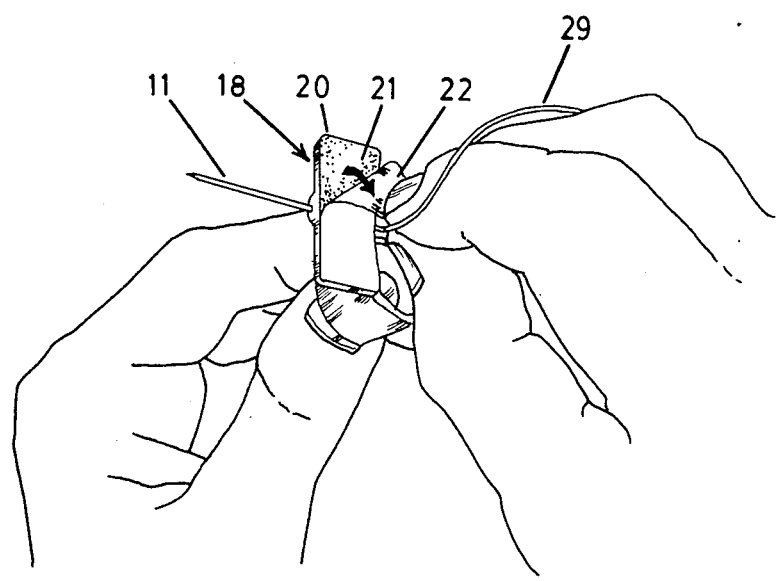
Figure 9:
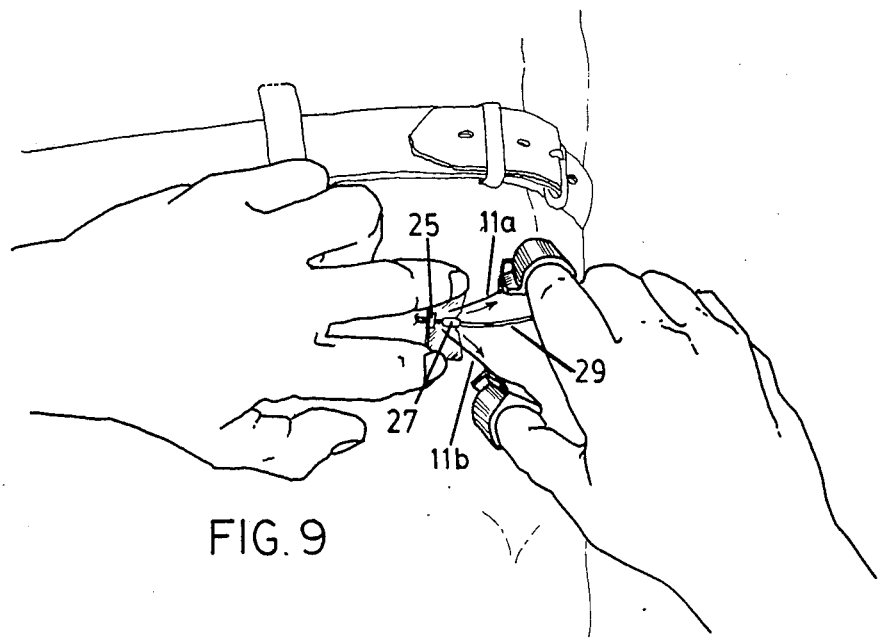
Figure 8:
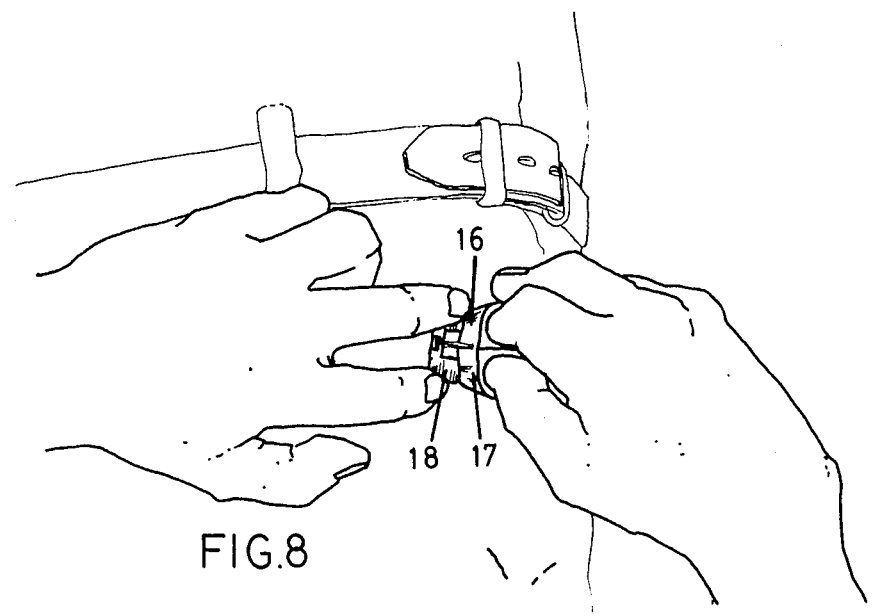

DESCRIPTION OF THE PREFERRED EMBODIMENTS:

The assembly 10 of this invention comprises a breakaway cannula needle and catheter, and is shown in FIGS. 1-3. Basically, the assembly inclucdes a needle portion 11, providing a tip portion 12 having a leading edge 12a, and split proximal ends 13a, 13b. Typically, the needle is about 24 gauge, or smaller. The proximal ends of the needle are secured by snap connections 14 to a metal or plastic base 15 that extends into circular finger grip elements 16, 17.

The base 15 is removeably mounted medially on catheter taping wings 18 along the upper side 19. The lower side 20 of the taping wings is coated with an adhesive 21 which is covered with a label 22 that is removed just prior to use. Positioned forwardly of the base is a holder 25 defining a central bore 26 which mounts the needle, and through which the needle is retracted following insertion into a patient or user.

As shown in FIGS. 1, 4 and 5, the rearward portion of the catheter taping wings 18 provides a plastic pad 27 defining a bore 28. A catheter 29 (of say, polyurethane) is bonded or otherwise secured within the bore 28, and extends through the needle to the trailing edge 12b of the needle tip 12. Hence, when the cannula needle is retracted from the user, the catheter will be secured within the bore 26 of holder 25 and the bore 28 of pad 27. As shown in FIGS. 1 and 5, a recessed space 30 is defined between the holder 25 and the pad 27, and the base 15 is fitted somewhat loosely in this space. The loose fit enables the user to pull the base 15 against the leading edge 27a of the pad 27, thereby splitting the needle.

Preferably, the entire assembly 10 is fitted together at the factory, packaged and sterilized, and then shipped for use. This procedure eliminates the need for assembly by the user and reduces the possibility of significant contamination.

FIGS. 6-9 illustrate use of the assembly employing only one hand. Using two fingers inserted into the finger grip elements 16, 17, the label 22 is removed from the lower side 20 of the catheter taping wings 18. The cannula needle 11 is inserted into the user or patient, say into a vein, or just under the surface of the skin. The catheter 29 extends into the needle up to the trailing edge 12b of the needle tip 12. Hence, when the needle is removed from the vein, the catheter will remain in place in the space created by the needle.

With the needle in place, the catheter taping wings 18 are pressed onto the user's skin. This will cause the taping wings, and hence the catheter, to be adhesively secured to the user. The needle is removed from the puncture site, and simultaneously, the needle is split against the pad 27. The needle halves 11a, 11b are then separated from the catheter. A metering pump, syringe, etc., is then attached to the catheter for injection of a pharmaceutical into the user.

The assembly of the breakaway needle and catheter of this invention facilitates self injection by a user, and can be used in conjunction with various types of delivery systems.

The assembly is inexpensive, and does not require treatment at a physician's office or hospital which is expensive and inconvenient. This gives users a psychological benefit since they are not constrained to reside near the physician's office, hospital, outpatient's clinic, etc., for treatment.

We claim:

1. A single hand operable assembly of a breakaway needle and catheter, comprising:
    a. a splittable cannula needle providing separated proximal ends and a needle tip;
    b. a splittable base for supporting the proximal ends of said splittable cannula and attached thereto;
    c. finger grips extending from the base, each grip being formed with an opening and adapted for gripping with fingers of one hand by a user;
    d. taping wings supporting and attached to the base, the taping wings being adapted for attachment to a user's body;
    e. catheter support means attached to the taping wings and positioned forwardly of said base;
    f. base splitting means attached to the taping wings and located rearwardly of said catheter support means and spaced therefrom to position said base between said catheter support means and said base splitting means for splitting said base and said cannula upon retraction of said base and said cannula from said support means towards said base splitting means; and,
    g. a catheter extending within the needle to the needle tip, the catheter being secured to the taping wings by the catheter support means; whereby:
        i. when the finger grips are gripped by a user, the needle and catheter can be simultaneously inserted into the user's body to form a puncture site; ii. upon retraction of the needle, the base and needle are adapted to be split against the base splitting means and separated from the catheter; iii. the catheter will remain in the puncture site; and, iv. the taping wings and attached catheter are adapted to be secured to the user's body.

2. The assembly of claim 1, wherein said catheter support means and said base splitting means each define a bore, and the catheter is secured with at least one bore.

3. The assembly of claim 2, in which said base splitting means is adapted to split the needle when the needle is retracted into contact with said base splitting means.

4. The assembly of claim 1, providing an adhesive coating on the taping wings for securing the wings to the user.

5. The assembly of claim 1, in which the needle is less than about 24 gauge.

* * * * *